United States Patent
Carnali et al.

(10) Patent No.: US 7,671,007 B2
(45) Date of Patent: Mar. 2, 2010

(54) PERSONAL CARE COMPOSITIONS COMPRISING HYDROPHOBICALLY MODIFIED CATIONIC POLYMERS

(75) Inventors: Joseph Oreste Carnali, Newtown, CT (US); Pravin Shah, Rutherford, NJ (US); Jack Polonka, Peekskill, NY (US); Stephen Alan Madison, Newtown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 365 days.

(21) Appl. No.: 11/418,513

(22) Filed: May 4, 2006

(65) Prior Publication Data

US 2007/0259795 A1 Nov. 8, 2007

(51) Int. Cl.
*C11D 3/37* (2006.01)
(52) U.S. Cl. ...................................... 510/475
(58) Field of Classification Search ................. 510/475
See application file for complete search history.

(56) References Cited

U.S. PATENT DOCUMENTS

| | | | | | |
|---|---|---|---|---|---|
| 4,454,060 | A | * | 6/1984 | Lai et al. | 510/429 |
| 5,362,827 | A | * | 11/1994 | Bock et al. | 526/219.2 |
| 6,299,868 | B1 | * | 10/2001 | Jozefiak et al. | 424/78.35 |
| 6,482,402 | B1 | * | 11/2002 | Kurtz et al. | 424/78.17 |
| 2001/0036912 | A1 | * | 11/2001 | Shulman et al. | 510/475 |
| 2006/0266488 | A1 | * | 11/2006 | Doherty et al. | 162/164.1 |

FOREIGN PATENT DOCUMENTS

| | | |
|---|---|---|
| EP | 1 524 270 | 4/2005 |
| WO | 2004/103327 | 12/2004 |

OTHER PUBLICATIONS

International Preliminary Report on Patentability on International Application No. PCT/EP2007/053409 dated Oct. 20, 2008.

* cited by examiner

*Primary Examiner*—John R Hardee
(74) *Attorney, Agent, or Firm*—Edward A. Squillante, Jr.

(57) ABSTRACT

The invention provides personal care/personal wash compositions comprising hydrophobically modified cationic polymers which enhance deposition of benefit agent.

8 Claims, No Drawings

PERSONAL CARE COMPOSITIONS COMPRISING HYDROPHOBICALLY MODIFIED CATIONIC POLYMERS

FIELD OF THE INVENTION

The present invention relates to personal care compositions (e.g., bars, liquids, creams, lotions), particularly personal wash-off and rinse-off compositions (rinse-off bars or liquids) comprising hydrophobically modified cationic polymers. More particularly, the invention is directed to cationic polymers which have sufficient charge density and are modified in such way as to interact directly with benefit agents (e.g., optical modifier particles such as mica or talc; polar and non-polar oils) without the necessity of interaction with anionic surfactants, to enhance deposition of the benefit agents from personal wash compositions.

BACKGROUND OF THE INVENTION

The use of cationic polymers to enhance deposition of particles has been disclosed, for example, by applicants. In several of applicants' co-pending applications (e.g., U.S. Ser. No. 10/997,179 to Tsaur et al.; U.S. Ser. No. 10/997,180 to Patel et al.; U.S. Ser. No. 11/043,509 to Polonka et al.), for example, applicants disclose compositions comprising cationic polymer as part of a deposition system for delivering particles providing optical benefits. In these applications, however, cationic polymers interact with anionic surfactant to form a precipitate or coacervate which enhances deposition of particles.

In co-pending U.S. Ser. Nos. 11/370,109 and 11/370,267, both to Polonka et al., the "deposition system" (cationic polymer/anionic surfactant) forms individually on particles to be deposited. The thus "coated" particles interact with air to form a foam lather structure and particles are deposited predominantly from lather in use. The individual deposition system chemistry still, however, is dependent on anionic surfactant interacting with cationic particles. None of the above references disclose use of hydrophobically modified cationic polymers to interact directly with benefit agent (e.g., benefit agent particles) without need of anionic surfactant as part of deposition system, to enhance benefit agent deposition. Benefit agents with which hydrophobically modified cationics can react can, in principle, include emulsions of silicones or oils. To the extent the emulsion is naturally negatively charged, it will interact with the modified cationic to enhance deposition.

U.S. Application No. 2004/0223993 to Clapp et al. disclose direct hydrophobic modification of particles, but not the use of such hydrophobically modified cationic polymers. U.S. Pat. No. 6,780,826 to Zhang discloses deposition of particles based on particle geometry.

In a reference entitled "Effects of low-level substitution on conditioning properties of cationic cellulosic polymers in shampoo systems", Journal of Cosmetic Science, volume 55, pages S195-S205 (2004), T. V. Drovetskaya et al. disclose quaternized hydroxyethylcellulose polymers having hydrophobic character due to grafting of dimethyl dodecyl ammonium groups onto the cellulose backbone. The product is known commercially as Polymer SL®. Cationic substitution is achieved with trimethyl ammonium grafts.

In Polymer SL®, the degree of cationic substitution is fixed as 0.2, meaning that one in five anhydroglucose units contains a quaternized graft. This level of modified cation corresponds to 1% nitrogen. Since the repeat unit molecular weight for a cellulose backbone with this level of cationic grafts is about 300, this material has a cationic charge density of 0.7 milli-equivalents per gram.

Polymers of the subject invention typically have charge density >2 meq/g, preferably >2.5 meq/g, more preferably >4 meq/g.

Zhao et al. of Chinese Academy of Sciences published a paper entitled "Synthesis and Flocculation Properties of Poly (dialkyl dimethyl ammonium chloride-vinyl trimethoxysilane) and poly (diallyl dimethyl ammonium chloride-acrylamide-vinyl trimethoxysilane) in Journal of Applied Polymer Sciences, Volume 84, pp 335-342 (2002). The Zhao publication does not teach or suggest use of hydrophobically modified cationic polymers in personal care compositions and are only concerned with flocculants for water treatment. That is, although describing certain hydrophobically modified di and tri-block cationic polymers, the reference fails to disclose personal care, particularly personal wash wash-off and rinse-off compositions comprising cleansing surfactant (i.e., containing at least 5% surfactant) and/or benefit agents (e.g., optical modifier particles; or emulsions), or that the modified cationic polymer enhances deposition of particles (even in absence of specific anionics).

BRIEF SUMMARY OF THE INVENTION

Unexpectedly, applicants have found that hydrophobically modified cationic polymers of a charge density exceeding about 2 milli-equivalents per gram enhance deposition of benefiting agents in personal care cleansing compositions comprising at least about 5% cleansing surfactant.

More particularly, the invention comprises personal care cleansing compositions comprising:

(1) 0.5 to 85%, preferably 5 to 75% by wt. cleansing surfactant (i.e., surfactant providing detergency);
(2) 0.1 to 10% by wt., preferably 1 to 9% by wt. of a benefit agent;
(3) 0.01 to 5%, preferably 0.05 to 3% by wt. of a water-soluble (by water soluble is meant having solubility in water in excess of 0.1%) terpolymer having general structure:

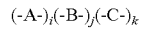

$$(-A-)_i(-B-)_j(-C-)_k$$

wherein co-monomer A represents a cationic repeating unit defined as possessing one or more cationic charges over the pH range 4 to 10; co-monomer B represents a water insoluble (by water insoluble is meant having a solubility in water which is less than 0.1%) repeating unit consisting of either a hydrophobic backbone or possessing a hydrophobic pendant group, in either case consisting of from 3 to 20 $C_1$ to $C_3$ alkylene (preferably methylene) groups, and from 1 to 3 $C_1$ to $C_3$ alkyl (preferably methyl) groups; and co-monomer C represents a repeating unit chosen so as to modify the overall polymer properties;

wherein the indices i, j, and k represent the number of times the respective monomer unit is repeated in the polymer chain, with the proviso that the ratio j/i is from about 0.01 to about 0.4 and that the ratio k/i is from about 0.0 to about 0.5;

and wherein co-monomer A has charge density $\geq 3$ meq/g and/or the terpolymer has charge density $\geq 2$ meq/g.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to personal care compositions comprising hydrophobically modified cationic polymers. The polymers have both a sufficiently large charge density (defined by co-monomer A having a charge density >3 milli-equivalents per gram, and/or the entire polymer having a charge density >2.0, preferably >2.5 milli-equivalents per gram); and sufficient hydrophobic modification (defined by a co-monomer B having a pendant group whose equivalent alkane carbon number (EACN) is >4 and present at such a level that the ratio of monomer B to monomer A lies in the range from about 0.01 to about 0.4) to enhance deposition of benefit agents from the personal care compositions. It is important to note that, notwithstanding the level of hydrophobic modification, the resulting polymer must still be water soluble.

With the noted charge densities and noted degree of hydrophobic modification, it is believed that the cationic polymers are able to interact directly with benefit agents (independent of whether or not they are formulated with anionic surfactant) to enhance deposition of the benefit agents. While previous art has contemplated use of cationic polymer to interact with anionic surfactant and help particle deposition; or contemplated hydrophobic modification of particles themselves to enhance particle deposition, to applicant's knowledge, the art has never contemplated directly modifying a cationic polymer, particularly a high charge density cationic, in order to enhance benefit agent deposition.

Specifically, the invention relates to cleansing compositions, i.e., composition comprising at least about 5% surfactant and further comprising the above noted cationic polymer and benefit agents.

The invention further relates to a method of enhancing deposition of benefit agents, particularly those providing an optical benefit (e.g., benefit agent particles), comprising formulating a composition comprising at least about 5% surfactant, benefit agent particle and the defined cationic polymer.

The various elements of the invention are set forth more specifically below.

Polymers

The hydrophobically modified polymers of the invention comprise terpolymers having the general structure:

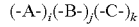

wherein co-monomer A is a cationic repeating unit possessing one or more cationic charge(s) when measured at a pH of 4 to 10;

wherein co-monomer B is a water insoluble (solubility in water of less than 0.1%) repeating unit comprising at least one hydrophobic portion which is part of the co-monomer backbone or a pendant group attached to the backbone and which hydrophobic portion is defined as comprising 3 to 20 $C_1$ to $C_3$, preferably $C_1$, alkylene groups and from 1 to 3 $C_1$ to $C_3$, preferably $C_1$ alkyl groups such that equivalent alkane carbon number (EACN) of the pendant group is >4, wherein co-monomer C is a repeating unit selected to modify solubility (preferably make more water soluble) of the overall polymer;

wherein i, j, and k represent the number of times each respective monomer is repeated in the polymer claim, with the proviso that ratio of j/i is from 0.01 to 0.4 and ratio of k/i is from 0.0 to 0.5 and such that the sum of i+j+k falls into the broad range of 100 (MW~10,000) to 20,000 (MW~$10^6$).

It is an important aspect of the invention that the modified cationic polymer have both sufficient charge density and hydrophobic modification to be able to provide a deposition chemistry (e.g., through interacting of modified cationic and benefit agent) for benefit agent (e.g., particles, emulsions) which might be present in compositions in which the modified cationic polymer may be used.

Thus, preferably the cationic charge density of co-monomer A should be at >3 milli equivalents of charge per gram of monomer units, more preferably >4 meq/gm, more preferably >5 meq/gm and even more preferably >6 meq/gm; and/or the density of the entire polymer should be >2, preferably >2.5 meq/gm.

The polymer is preferably chosen so ratio of i (representing monomer A) to i+j+k will yield charge density >2, preferably >2.5 meq/gm per total polymer.

The copolymer preferably is also chosen such that repeating unit B has a pendant side chain carrying an EACN of at least 4, more preferably of at least 8, most preferably of at least 10. As an upper limit the pendant chain would likely have an EACN of 18 or less, as higher EACN chains are difficult to copolymerize and would render the resulting copolymer water insoluble.

The equivalent alkane carbon number concept was introduced by L. Cash et al., in "The application of low interfacial tension scaling rules to binary hydrocarbon mixtures", Journal of Colloid and Interface Science, volume 59, pages 39-44, 1977. The interfacial tension of water with mixtures of oils was correlated by these authors using the EACN to describe the oil mixture as follows: EACN=$X_A$ EACN$_A$+$X_B$ EACN$_B$. Here $X_A$ and $X_B$ are the mole fractions of oil component A and B, respectively, each oil being described by an individual EACN. This EACN is in turn described as the number of carbons in the longest, linear segment that can be identified in a cyclic or non-linear oil. The EACN concept is a convenient way to compare linear and non-linear oils in terms of their interaction with water.

The copolymer is further preferably chosen and nature of B selected such that ratio of j to i falls into the range of about 0.01 to about 0.4 (keeping in mind that the resulting polymer must still be water soluble).

The copolymer may further be further selected so that repeating C unit partially replaces unit B in order to make the polymer more water soluble.

In a preferred embodiment, the sum of i+j+k corresponds to polymer having molecular wt. in range of 10,000 to 2,000,000.

As indicated co-monomer C is optional (controls water solubility depending on hydrophobicity which is established through co-monomer B) and, in one embodiment, the ratio of k/i can be effectively zero. In another preferred embodiment, C is chosen to have an amine functionality. It is believed that amine functionality can promote peptide bonding/binding with the proteins/amino acids on skin and so improve substantivity.

Cationic Monomers corresponding to repeating unit A can be chosen, for example, from a list including 2-acryloxyethyl trimethyl ammonium chloride (AETAC), methacryloxyethyl trimethyl ammonium chloride (METAC), dimethyl diallyl ammonium chloride (DMDAAC), acrylamidopropyl trimethyl ammonium chloride (APTAC), methacrylamidopropyl trimethyl ammonium chloride (MAPTAC), and methyl quaternized vinyl imidazole.

Hydrophobic monomers corresponding to repeating unit B below can be chosen, for example, from a list including n-dodecyl methacrylamide (DMA), n-(n-octadecyl acrylamide) (ODA), and n-tert-octylacrylamide (tOA) and other. The EACN of the pendant groups on these co-monomers are DMA=12, ODA=8, and tOA=4.

Co-monomers corresponding to repeating unit C below can be chosen from any of the water-soluble monomers containing primary, secondary, or tertiary amine functional groups, including amides and imides, as well as alcohols. Such co-monomers include acrylamide, methacrylamide, dimethylacrylamide, isopropylacrylamide, acrylylglycinamide, methacrylylglycinamide, vinyl oxazolidone, vinyl methyloxazolidone, vinyl pyrrolidone, and vinyl alcohol.

Specifically, the invention comprises personal care compositions (e.g., bars, liquid, creams etc.), especially rinse-off personal wash compositions (e.g., bars, liquids) in which the co-polymers of the invention enhance deposition of benefiting agents, for example, optical benefit agent particles. Specifically, this embodiment of the invention comprises:

(1) 0.5 to 85%, preferably 3 to 80%, more preferably 5 to 75% by wt. of a cleansing surfactant;
(2) 0.1 to 10% by wt., preferably 1 to 9% by wt. of a benefit agent; and
(3) 0.01 to 5%, preferably 0.05 to 3% by wt. of a water-soluble terpolymer having the structure noted above and as defined above.

Surfactants

The surfactant can be any of the thousands of anionic surfactants, nonionic surfactants, amphoteric surfactants, zwitterionic surfactants cationic surfactants and mixtures clearly as are well known in the art.

Anionic surfactants include, but are certainly not limited to aliphatic sulphate, aliphatic sulfonate (e.g., $C_8$ to $C_{22}$ sulfonate or disulfonate), aromatic sulfonate (e.g., alkyl benzene sulfonate), alkyl sulfoccinates, alkyl and acyl taurates, alkyl and acyl sarcosinates, sulfoacetates, alkyl phosphates, carboxylates, isethionates, etc.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

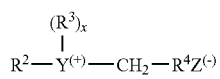

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom (note that when x is 2, the $R^3$ groups are attached to Y by two different bonds); $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

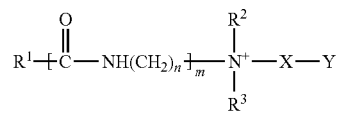

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $—CO_2—$ or $—SO_3—$ Nonionic Surfactants The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Indeed, one important aspect of the invention is the fact that it introduces formulation flexibility. That is, for example, the deposition system is not dependent on inclusion of anionic surfactant since high charge density, modified cationic will interact with benefit agent to form deposition system rather than requiring a cationic polymer/anionic surfactant deposition system. This in turn allows, for example, that much milder surfactants be used rather than rely on generally harsher (harsher on skin) anionic surfactants.

Benefit Agent

The benefit agent may be in principle any negatively charged moiety which will react with the hydrophobically modified cationic polymer. This may include, for example, emulsions of silicones or oils.

In a preferred embodiment, the benefit agent is an optical modifier which may be chosen from non-colored and colored, organic and inorganic materials.

Among the materials which may be used are included:

Organic pigments, inorganic pigments, polymers and fillers such as titanium oxide, zinc oxide, colored iron oxide, chromium oxide/hydroxide/hydrate, alumina, silica, zirconia, barium sulfate, silicates, natural/alkaloid (including derivatives) polymers, polyethylene, polypropylene, nylon, ultramarine, alkaline earth carbonates. The materials can be platy materials such as talc, sericite, mica, synthetic mica, platy substrate coated with organic and inorganic molecules, bismuth oxychloride, barium sulfate. Particle can be composed of several materials (like dyes, lakes, toners). Lakes are, for example, dyes with aluminum hydroxide to help bind to solid. Color can be generated through fluorescence, absorption or iridescence. That is, color of modifier materials is generated through optical means rather than, for example, chemical means.

Polymer

The polymer of the personal wash compositions is as described above.

In a second embodiment of the invention, the invention relates to a method of enhancing deposition of particles, particularly optical modifier particles, using the hydrophobically modified polymers of the invention.

EXAMPLES

The polymerization process of the invention can be noted as set forth below.

Hydrophobically modified cationic polymers are synthesized by copolymerizing X moles of a cationic monomer with Y moles of hydrophobic monomer in an alcoholic solvent. Here, the fractions X/(X+Y) and Y/(X+Y) then designate the mole fraction of cationic and hydrophobic monomers, respectively, in the feed stock. The alcoholic solvent was a blend of ethanol and methanol, selected so as to be a good solvent for both the cationic and hydrophobic monomers, and contained 5-20% w/w of water by virtue of the fact that the cationic monomers employed were added as concentrated aqueous solutions. The monomers and solvent were charged into a round bottom flask and the solution was deaerated by purging with nitrogen for thirty minutes. At this point, polymerization was initiated by addition of initiator and heating under reflux using a heating mantle and a water-cooled condenser. The initiator was used at a level of 0.01-0.5 grams per hundred grams of monomer and was dosed incrementally at equally spaced intervals depending upon the half-life of the initiator and the total time of the polymerization. At the end of the polymerization, the volume of the reaction mixture was reduced to about ½ by evaporation of alcohol under a nitrogen stream and then diluted with water. Unreacted monomer, initiator and solvent were removed by dialyzing the reaction mixture against distilled/ deionized water using a Spectra/Por 3® dialysis membrane with a 3500 molecular weight cut-off. Water was than removed by freeze-drying to leave the copolymer as a fine powder. The actual copolymer composition of the product was determined by $^1$H NMR spectroscopy of a solution in $D_2O$.

Measurement of Deposition Using Contact Angle Test

Modification of the contact angle of water on glass: Glass microscope slides are cleaned by soaking for fifteen minutes in hot 70% nitric acid and are then rinsed extensively in distilled-deionized water to give a substrate possessing a zero contact angle with respect to water. The slides are then immersed for a period of sixty seconds in a 0.1% aqueous solution of the polymer to be tested. Following immersion, the slides are removed from the solution and rinsed in running distilled-deionized water for ten seconds on each side. This rinsing protocol is repeated for a total of three cycles and then the slides are patted dry with an optical quality absorbent wiper. The slides are then mounted on a Rame Hart contact angle goniometer and a droplet of water applied using a micro-syringe. The contact angle which the droplet makes with the glass substrate is read via a microscope against a protractor scale. The measurement was repeated on five droplets, using a new droplet on a different portion of the substrate for each determination. The average value is then reported.

Examples 1-5

Preparation of Various Vinyl Polymers

Example 1

90/10 mole ratio feed of dimethyl diallyl ammonium chloride (DMDAAC)/N-tert-Octyl acrylamide (tOA). A 50 mL three-necked flask was charged with 45 milli-moles DMDAAC (MW 161.6, 11.19 g of a 65% aqueous solution) and 5 milli-moles of tOA (MW 183.3, 0.9165 g dissolved in 10 mL methanol). An additional 10 mL of methanol was added, containing 4% ethanol to raise the boiling point of the solvent (BP of MeOH=60° C. and B.P of EtOH=76° C.). The flask was fitted with a condenser and purged with dry nitrogen for thirty minutes. A heating mantle was then applied and the mixture heated to reflux (68° C.). The initiator employed was 2,2' azobisisobutyro nitrile dissolved in MeOH at a level of 0.3% w/w based on the monomers. In this case, 36.3 mg (0.003×(11.19+0.9165)) was dissolved in 10 mL of methanol and was added to the refluxing mixture in equal aliquots every 7 hours. The reaction was terminated after 72 hours and the product was isolated as described above. The co-monomer molar ratio in the final product was determined by $^1$H NMR to be 86/14 DMDAAC/tOA.

Example 2

88/12 mole ratio feed of dimethyl diallyl ammonium chloride (DMDAAC)/N-tert-Octyl acrylamide (tOA). A 50 mL three-necked flask was charged with 44 milli-moles DMDAAC (MW 161.6, 10.95 g of a 65% aqueous solution) and 6 milli-moles of tOA (MW 183.3, 1.0974 g dissolved in 10 mL methanol). An additional 10 mL of methanol was added, containing 4% ethanol to raise the boiling point of the solvent (BP of MeOH=60° C. and B.P of EtOH=76° C.). The flask was fitted with a condenser and purged with dry nitrogen for thirty minutes. A heating mantle was then applied and the mixture heated to reflux (68° C.). The initiator employed was 2,2 azobisisobutyro nitrile dissolved in MeOH at a level of 0.25% w/w based on the monomers. In this case, 30 mg (0.0025×(10.95+1.0974)) was dissolved in 10 mL of methanol and was added to the refluxing mixture in equal aliquots every 7 hours. The reaction was terminated after 72 hours and the product isolated as described above. The co-monomer molar ratio in the final product was determined by $^1$H NMR to be 81/19 DMDAAC/tOA.

Example 3

85/15 mole ratio feed of dimethyl diallyl ammonium chloride (DMDAAC)/N-tert-Octyl acrylamide (tOA). A 50 mL three-necked flask was charged with 42.5 milli-moles DMDAAC (MW 161.6, 10.56 g of a 65% aqueous solution) and 7.5 milli-moles of tOA (MW 183.3, 1.375 g dissolved in 10 mL methanol). An additional 10 mL of methanol was added, containing 4% ethanol to raise the boiling point of the solvent (BP of MeOH=60° C. and B.P of EtOH=76° C.). The flask was fitted with a condenser and purged with dry nitrogen for thirty minutes. A heating mantle was then applied and the mixture heated to reflux (68° C.). The initiator employed was 2,2 azobisisobutyro nitrile dissolved in MeOH at a level of 0.3% w/w based on the monomers. In this case, 36 mg (0.003×(10.56+1.375)) was dissolved in 10 mL of methanol and was added to the refluxing mixture in equal aliquots every 7 hours. The reaction was terminated after 72 hours and the product isolated as described above. The co-monomer molar ratio in the final product was determined by $^1$H NMR to be 80/20 DMDAAC/tOA.

Example 4

80/20 mole ratio feed of dimethyl diallyl ammonium chloride (DMDAAC)/N-tert-Octyl acrylamide (tOA). A 50 mL three-necked flask was charged with 40 milli-moles DMDAAC (MW 161.6, 9.945 g of a 65% aqueous solution) and 10 milli-moles of tOA (MW 183.3, 1.833 g dissolved in 10 mL methanol). An additional 10 mL of methanol was added, containing 4% ethanol to raise the boiling point of the solvent (BP of MeOH=60° C. and B.P of EtOH=76° C.). The flask was fitted with a condenser and purged with dry nitrogen for thirty minutes. A heating mantle was then applied and the mixture heated to reflux (68° C.). The initiator employed was 2,2 azobisisobutyro nitrile dissolved in MeOH at a level of 0.3% w/w based on the monomers. In this case, 35.3 mg (0.003×(9.945+1.833)) was dissolved in 10 mL of methanol and was added to the refluxing mixture in equal aliquots every 7 hours. The reaction was terminated after 72 hours and the product isolated as described above. The co-monomer molar ratio in the final product was determined by $^1$H NMR to be 70/30 DMDAAC/tOA.

Example 5

90/10 mole ratio feed of 2-acryloxyethyl trimethyl ammonium chloride (AETAC)/n-dodecyl methacrylamide (DMA). A 50 mL three-necked flask was charged with 45 milli-moles AETAC (MW 193.6, 10.89 g of a 80% aqueous solution) and 5 milli-moles of DMA (MW 253.4, 1.267 g dissolved in 10 mL ethanol). An additional 10 mL of ethanol was added (B.P of EtOH=76° C.) and the flask was fitted with a condenser and purged with dry nitrogen for thirty minutes. A heating mantle was then applied and the mixture heated to reflux (76° C.). The initiator employed was 2,2 azobisisobutyro nitrile dissolved in ethanol at a level of 0.3% w/w based on the monomers. In this case, 36.5 mg (0.003×(10.89+1.267)) was dissolved in 10 mL of ethanol and was added to the refluxing mixture in equal aliquots every 7 hours. The reaction was terminated after 72 hours and the product isolated as described above. The co-monomer molar ratio in the final product was determined by $^1$H NMR to be 89/11 AETAC/DMA.

In addition to the vinyl polymers of Example 1-5 synthesized above, a series of hydrophobically modified hydroxyethyl cellulose polymers were also obtained as samples from Amerchol Corporation (A subsidiary of the Dow Company). The material designated as SoftCAT Polymer SK-M® was described as a high viscosity, quaternized hydroxyethyl cellulose polymer which has been substituted with trimethyl ammonium groups. The nitrogen weight percentage of this material has been determined as 1.1% and, assuming an average of 2.5 moles of ethylene oxide per anhydroglucose ring, the degree of cationic substitution can be estimated at 0.22 with a cationic charge density of 0.8 milli-equivalents per gram. A hydrophobically modified hydroxyethyl cellulose was provided as SK-MH®, with a nitrogen weight percentage of 1.0% and consequently the same degree of substitution and a charge density of 0.7 milli-equivalents per gram. According to the manufacturers, SoftCAT SK-MH® also contained a low level of hydrophobic dimethyldodecyl ammonium substitution. Applicants have employed $^1$H NMR to estimate that the level of hydrophobic loading on this polymer to corresponds to two (2) hydrophobic units per 100 anhydroglucose rings. Both materials are water soluble, but they also are both highly effective at increasing the viscosity of water.

Example of Deposition—Contact Angle Test

The ability of the copolymers constituting the present invention to improve the deposition of skin benefiting agents was demonstrated using the contact angle test described in the protocol above.

The results of the contact test are set forth in Table 1 below:

TABLE I

| Contact angle of water drops on polymer treated glass slides. | |
|---|---|
| Polymer used in treatment (co-monomer feed ratio) | Contact angle, degrees (avg.) |
| Merquat 100 * (Comparative) | 13.2 ± 2.0 |
| Example 1 (90/10 ratio) | 20.4 ± 2.0 |
| Example 2 (88/12 ratio) | 27.4 ± 3.0 |
| Example 3 (85/15 ratio) | 30.4 ± 3.0 |
| Example 5 (90/10 ratio) | 18.5 ± 2.0 |
| SK-M (Comparative) | 17.5 ± 2.0 |
| SK-MH | 21.8 ± 2.0 |

* Merquat 100 is a 200,000 molecular weight homopolymer of dimethyl diallyl ammonium chloride (DMDAAC) manufactured by Nalco Corp.

The results of Table I indicate that successively more hydrophobically modified polymers, examples 1⇒2⇒3, have a progressively greater tendency to increase the contact angle of water on the surface of glass. Such an increase is consistent with the polymer hydrophobing the glass surface. The slight hydrophobic character of SK-MH nonetheless shows the same tendency to increase the contact angle with respect to SK-M.

Example of Deposition—Change in Optical Values

The polymers of the present invention were incorporated into beauty bars corresponding to the following composition.

|  | Example | | | | |
| --- | --- | --- | --- | --- | --- |
| Composition | 6 | 7 | 8 | 9 | 10 |
| Sodium laurate | 15 | 15 | 15 | 15 | 15 |
| Sodium dodecyl sulfate | 2 | 2 | 2 | 2 | 2 |
| Sucrose | 45 | 45 | 45 | 45 | 45 |
| Maltodextrin | 15 | 15 | 15 | 15 | 15 |
| TCM Polymer (Titanium Coated Mica) | 5 | 5 | 5 | 5 | 5 |
| Merquat 100 * (Comparative) | 0.4 | | | | |
| Polymer of Example 1 (90:10 DMDAAC/tOA) | | 0.4 | | | |
| Polymer of Example 3 (85:15 DMDAAC/tOA) | | | 0.4 | | |
| SK-M (Comparative) | | | | 0.4 | |
| SK-MH | | | | | 0.4 |
| Water to balance | | | | | |

* Merquat 100 is a 200,000 molecular weight homopolymer of dimethyl diallyl ammonium chloride (DMDAAC) manufactured by Nalco Corp.

The deposition of titanium coated mica (TCM) particles from these bars onto pig skin was gauged via a protocol which can be summarized as follows. The pig skin was obtained from black female skin, 3-5 months old, partly shaved and dermatomed to 1.5 mm. Each piece of skin measured 1"×3" and was adhered to a glossy card. A lather of approximately 100 mL volume was generated by wetting and rubbing the bar under running tap water. The lather was transferred to the piece of pig skin and worked into the skin for 60 seconds before rinsing for 30 seconds under running tap water. The skin was allowed to dry for 1 hour before the change in reflectivity of the skin was read with a Glossmeter (Novo-Gloss Statistical Gloss Meter).

TABLE II

Reflectivity of skin samples treated with lather.

| Polymer used in treatment | % change in reflectivity value (avg.) | Delta L |
| --- | --- | --- |
| Example 6 (Comparative) | 85 | 1.8 |
| Example 7 | 93 | 4.8 |
| Example 8 | 120 | 10.6 |
| Example 9 (Comparative) | 24 | 0.2 |
| Example 10 | 66 | 5.1 |

The higher level of reflectivity reported with the more hydrophobically modified polymers, examples 7 and 8 versus the comparative example 6, indicates that the modification serves to increase the level of particle deposition from the bars. Similarly, example 10 gives a benefit over comparative example 9.

The invention claimed is:

1. A personal wash (care) liquid, cream or lotion composition comprising:
  (a) 0.5 to 85% by wt. of a cleansing surfactant;
  (b) 0.1 to 10% by wt. of an optical modifying benefit agent;
  (c) 0.01 to 5% by wt. of a polymer having structure

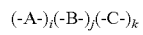

$(-A-)_i(-B-)_j(-C-)_k$ wherein co-monomer A is a cationic repeating unit possessing one or more cationic charge(s) when measured at pH 4 to 10;
  wherein co-monomer B is a water insoluble repeating unit comprising at least one hydrophobic portion which is part of the co-monomer backbone which hydrophobic portion is defined as comprising 3 to 20 $C_1$ to $C_3$ alkylene groups and from 1 to 3 $C_1$ to $C_3$ alkyl groups and/or a pendant attached to the backbone such that equivalent alkane number of pendent group is >4 and wherein B is selected from the group consisting of n-dodecyl methacrylamide (DMA), n-(n-octadecylacrylamide) (ODA), n-tert-octylacrylamide (tOA) and mixtures thereof;
  wherein co-monomer C is a repeating unit selected to modify solubility of the overall polymer;
  wherein i, j, and k represent number of times each respective monomer is repeated in the polymer chain, with the proviso that ratio of j/i is from 0.01 to 0.4 and ratio of k/i is from 0.0 to 0.5; and
  wherein cationic charge density of co-monomer A is >3 meq/g; and/or charge density of entire polymer >2.

2. A composition according to claim 1, wherein the co-monomer B of the polymer is chosen to have equivalent alkaline carbon number (EACN) of >8.

3. A composition according to claim 1, in which the repeating unit co-monomer C is used to increase the water solubility of the resulting polymer.

4. A composition according to claim 1, in which the sum of indices i, j, and k of the polymer corresponds to a polymer whose molecular weight is in the range of 10,000 to 2,000,000.

5. A composition according to claim 1, in which the nature of co-monomer A of the polymer and the ratio of index i to the sum of i plus j plus k corresponds to a polymer cationic charge density of at least 2.5 milli-equivalents of charge per gram of polymer.

6. A composition according to claim 1, in which the nature of co-monomer B of the polymer and the ratio of index j to the sum of indices i plus j plus k corresponds to a polymer which retains a water solubility in excess of 0.1%.

7. A composition according to claim 1, wherein the benefit agent is a solid particulate substance.

8. A personal wash composition according to claim 1, in which the ratio in the polymer of k/i is effectively zero.

* * * * *